United States Patent
McVeigh et al.

(10) Patent No.: US 10,448,901 B2
(45) Date of Patent: Oct. 22, 2019

(54) METHODS FOR EVALUATING REGIONAL CARDIAC FUNCTION AND DYSSYNCHRONY FROM A DYNAMIC IMAGING MODALITY USING ENDOCARDIAL MOTION

(71) Applicant: THE JOHNS HOPKINS UNIVERSITY, Baltimore, MD (US)

(72) Inventors: Elliot Ross McVeigh, Timonium, MD (US); Amir Pourmorteza, Baltimore, MD (US)

(73) Assignee: The Johns Hopkins University, Baltimore, MD (US)

(*) Notice: Subject to any disclaimer, the term of this patent is extended or adjusted under 35 U.S.C. 154(b) by 0 days.

(21) Appl. No.: 14/350,991

(22) PCT Filed: Oct. 12, 2012

(86) PCT No.: PCT/US2012/060007
§ 371 (c)(1),
(2) Date: Apr. 10, 2014

(87) PCT Pub. No.: WO2013/056082
PCT Pub. Date: Apr. 18, 2013

(65) Prior Publication Data
US 2014/0257083 A1    Sep. 11, 2014

Related U.S. Application Data

(60) Provisional application No. 61/546,311, filed on Oct. 12, 2011.

(51) Int. Cl.
*A61B 5/00* (2006.01)
*A61B 5/02* (2006.01)
(Continued)

(52) U.S. Cl.
CPC .......... *A61B 5/7282* (2013.01); *A61B 5/0044* (2013.01); *A61B 5/0073* (2013.01);
(Continued)

(58) Field of Classification Search
CPC .......... A61B 5/055; A61B 5/7782; A61B 6/03; A61B 5/0044; A61B 5/0073; A61B 5/02;
(Continued)

(56) References Cited

U.S. PATENT DOCUMENTS 6,650,927 B1    11/2003    Keidar
7,415,093 B2 *    8/2008    Tkaczyk ................ A61B 6/541
378/4

(Continued)

FOREIGN PATENT DOCUMENTS

EP    1050272 A1    11/2000
EP    2372639 A1    10/2011
(Continued)

OTHER PUBLICATIONS

Seo, Yoshihiro, et al. "Endocardial surface area tracking for assessment of regional LV wall deformation with 3D speckle tracking imaging." JACC: Cardiovascular Imaging 4.4 (2011): 358-365.*
(Continued)

*Primary Examiner* — Carolyn A Pehlke
(74) *Attorney, Agent, or Firm* — Harrity & Harrity, LLP

(57) ABSTRACT

An embodiment in accordance with the present invention provides a method and system for evaluating regional cardiac function and dyssynchrony from an imaging modality using the motion of endocardial features of the heart. In the method and system, an imaging modality such as a CT scanner is used to obtain an image sequence that is then processed using a computer program. The computer program is configured to create an endocardial mesh formed from triangular components that represents at least the
(Continued)

region of interest of the subject's heart. From tracking the motion of conserved topological features on this endocardial mesh at least two time points a displacement map can be modeled. The displacement map can be further analyzed to determine metrics of regional cardiac function such as SQUEEZ, myocardial strain, torsion etc., and the displacement map can also be used to create visual representations of the function of the subject's heart.

22 Claims, 8 Drawing Sheets

(51) Int. Cl.
A61B 6/03 (2006.01)
A61B 6/00 (2006.01)
A61B 5/055 (2006.01)
A61B 5/11 (2006.01)
G06T 7/246 (2017.01)

(52) U.S. Cl.
CPC .......... A61B 5/02 (2013.01); A61B 5/02028 (2013.01); A61B 5/055 (2013.01); A61B 5/1128 (2013.01); A61B 5/4884 (2013.01); A61B 5/742 (2013.01); A61B 6/032 (2013.01); A61B 6/503 (2013.01); A61B 6/5217 (2013.01); A61B 6/5288 (2013.01); G06T 7/246 (2017.01); A61B 5/0035 (2013.01); A61B 6/037 (2013.01); A61B 2576/023 (2013.01); G06T 2207/10016 (2013.01); G06T 2207/10081 (2013.01); G06T 2207/30048 (2013.01)

(58) Field of Classification Search
CPC . A61B 5/02028; A61B 5/1128; A61B 5/4884; A61B 5/742; A61B 6/032; A61B 6/503; A61B 6/5217; A61B 6/5288; G06T 7/0012; G06T 7/246
USPC .................. 600/407, 410, 425; 382/128–132
See application file for complete search history.

(56) References Cited

U.S. PATENT DOCUMENTS

| 8,379,950 | B2 | 2/2013 | Ye et al. |
|---|---|---|---|
| 10,058,257 | B2 | 8/2018 | Miyazaki et al. |
| 2003/0097219 | A1* | 5/2003 | O'Donnell ............ G06T 7/0012 702/19 |
| 2004/0153128 | A1 | 8/2004 | Suresh et al. |
| 2010/0274123 | A1 | 10/2010 | Voth |
| 2010/0305433 | A1 | 12/2010 | Harlev et al. |

FOREIGN PATENT DOCUMENTS

| JP | 2009153677 A | 11/2004 |
|---|---|---|
| JP | 2004313291 A | 7/2009 |
| JP | 2011083592 | 9/2009 |
| JP | 2011177517 | 3/2010 |
| WO | 99/55233 A1 | 11/1999 |
| WO | 00/48511 A1 | 8/2000 |
| WO | 2004/037087 A2 | 5/2004 |
| WO | 2004/097720 A1 | 11/2004 |
| WO | 2005/004721 A1 | 1/2005 |
| WO | 2005/008583 A2 | 1/2005 |
| WO | 2006/066122 A2 | 6/2006 |
| WO | 2006/115567 A1 | 11/2006 |
| WO | 2007/004026 A1 | 1/2007 |
| WO | 2009/089341 A1 | 7/2009 |
| WO | 2010/046838 A1 | 4/2010 |
| WO | 2010/109343 A1 | 9/2010 |
| WO | 2011/070465 A2 | 6/2011 |

OTHER PUBLICATIONS

Frangi, Alejandro F. "Three-dimensional model-based analysis of vascular and cardiac images." (2001).*
Human Body Reading (Anatomical Imaging, http://www.mhhe.com/biosci/ap/vander/humbody/reading1.mhtml, Dec. 23, 2000).*
Weisstein, Eric W. "Regular Tessellation." From MathWorld—A Wolfram Web Resource http://mathworld.wolfram.com/RegularTessellation.html, Feb. 18, 2010.*
Myronenko, Andriy, Xubo Song, and Miguel A. Carreira-Perpinan. "Non-rigid point set registration: Coherent point drift." Advances in Neural Information Processing Systems. 2006.*
Dagianti, Armando, et al. "Stress echocardiography: comparison of exercise, dipyridamole and dobutamine in detecting and predicting the extent of coronary artery disease." Journal of the American College of Cardiology 26.1 (1995): 18-25.*
Willem Gorissen (Artida 3D Wall Motion Tracking, Aug. 2008).*
Gorissen, Willem. "An introduction to Area Tracking, a new parameter using 3D Wall Motion Tracking." 2009.*
What is Echocardiography (https://www.heart.org/idc/groups/heart-public/@wcm/@hcm/documents/downloadable/ucm_300438.pdf, Jul. 22, 2012).*
Meier, Dominik, and Elizabeth Fisher. "Parameter space warping: shape-based correspondence between morphologically different objects." IEEE Transactions on Medical Imaging 21.1 (2002): 31-47.*
Pourmorteza, Amir, Karl H. Schuleri, Daniel A. Herzka, Albert C. Lardo, and Elliot R. McVeigh. "A New Method for Cardiac Computed Tomography Regional Function AssessmentClinical Perspective: Stretch Quantifier for Endocardial Engraved Zones (SQUEEZ)." Circulation: Cardiovascular Imaging 5, No. 2 (2012): 243-250.*
Bill Dillinger (CK-12 Texas Instruments Geometry FlexBook, Unit 10 Perimeter and Area, http://www.newportsd.org/cms/lib/pa09000082/centricity/domain/127/unit_10_perimeter_and_area.pdf) May 12, 2011.*
Han, C., et al., (2012) "Noninvasive reconstruction of the three-dimensional ventricular activation sequence during pacing and ventricular tachycardia in the canine heart", American Journal of Physiology—Heart and Circulatory Physiology, 302(1), H244-H252.
Mischi, M., et al., (2011) "Three-dimensional quantification of regional left-ventricular dyssynchrony by magnetic resonance imaging", Paper presented at the Proceedings of the Annual International Conference of the IEEE Engineering in Medicine and Biology Society, EMBS, 2646-2649.
Kulp, S., et al., (2011) "Using high resolution cardiac CT data to model and visualize patient-specific interactions between trabeculae and blood flow", Medical Image Computing and Computer-Assisted Intervention : MICCAI . . . International Conference on Medical Image Computing and Computer-Assisted Intervention, 14(Pt 1), 468-475.
Po, M., et al., (2011) "Quantitative detection of left ventricular dyssynchrony from cardiac computed tomography angiography" Paper presented at the Proceedings—International Symposium on Biomedical Imaging, 1318-1321.
Mukhopadhyay, A., et al., (2011) "Shape analysis of the left ventricular endocardial surface and its application in detecting coronary artery disease" LNCS 6666, pp. 275-283.
Cosyns, B., et al., (2009) "Analysis of regional wall motion during contrast-enhanced dobutamine stress echocardiography: Effect of contrast imaging settings" European Journal of Echocardiography, 10(8), 956-960.
Lin, F., et al., (2012) "Physiological noise reduction using volumetric functional magnetic resonance inverse imaging" Human Brain Mapping, vol. 33, pp. 2815-2830.
Kuppahally, S., et al., (2011) "Dyssynchrony assessment with tissue doppler imaging and regional volumetric analysis by 3D echocardiography do not predict long-term response to cardiac resynchronization therapy" Cardiology Research and Practice, vol. 2011, Article ID 568918.
Gao, H., et al., (2011) "CMRI based 3D left ventricle motion analysis on patients with acute myocardial infarction" Paper presented at the Proceedings of the Annual International Conference of the IEEE Engineering in Medicine and Biology Society, EMBS, 6821-6824.

(56) References Cited

OTHER PUBLICATIONS

Weinsaft, J., et al., (2008) "Left ventricular papillary muscles and trabeculae are significant determinants of cardiac MRI volumetric measurements: Effects on clinical standards in patients with advanced systolic dysfunction" International Journal of Cardiology, vol. 126, No. 3, pp. 359-365.

Papademetris, X., (2002) "Estimation of 3-D left ventricular deformation from medical images using biomechanical models" IEEE Transactions on Medical Imaging, vol. 21, No. 7, pp. 786-800.

Shi, P., et al., (2000) Point-tracked quantitative analysis of left ventricular surface motion from 3-D image sequences IEEE Transactions on Medical Imaging, vol. 19, No. 1, pp. 36-50.

Seo, Y., et al., (2011) "Endocardial surface area tracking for assessment of regional LV wall deformation with 3D speckle tracking imaging" JACC: Cardiovascular Imaging, vol. 4, No. 4, pp. 358-365.

Extended European Search Report dated Mar. 24, 2015, for EP application 12839978.9.

\* cited by examiner

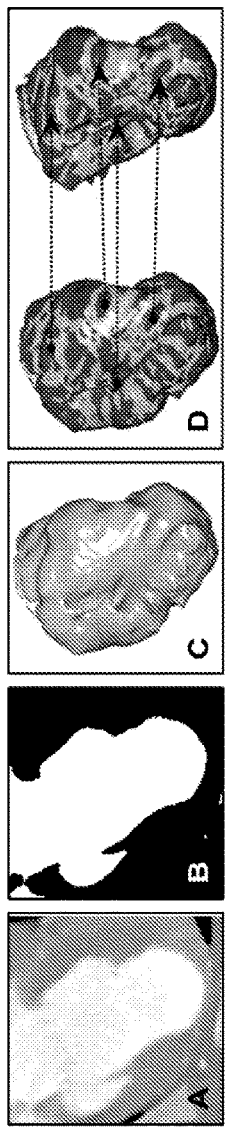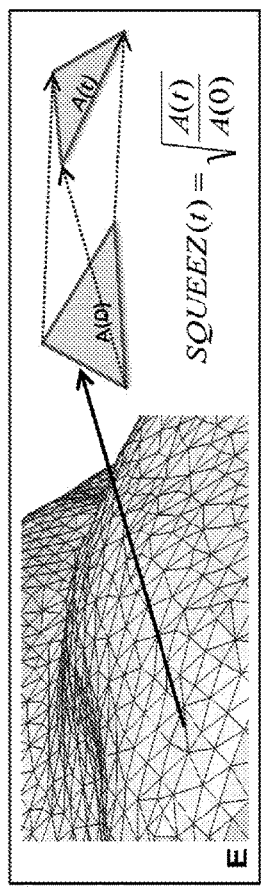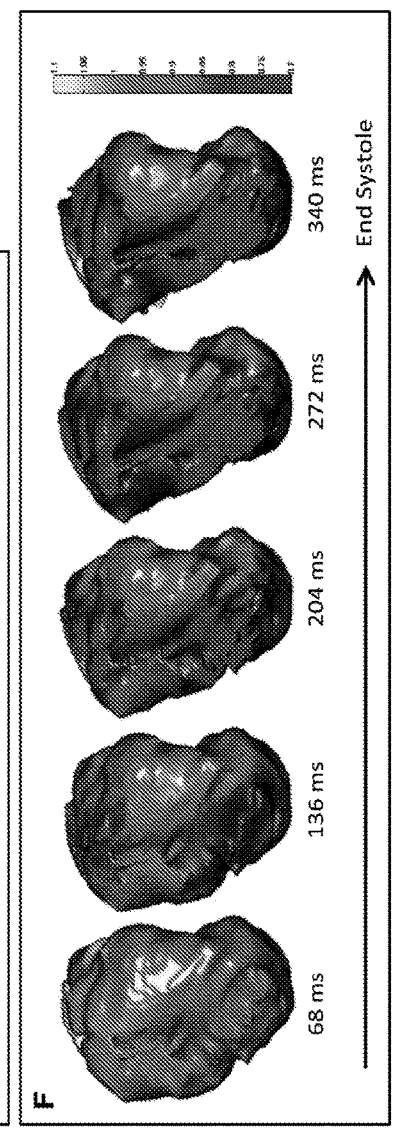
FIG. 3A  FIG. 3B  FIG. 3C  FIG. 3D  FIG. 3E  FIG. 3F

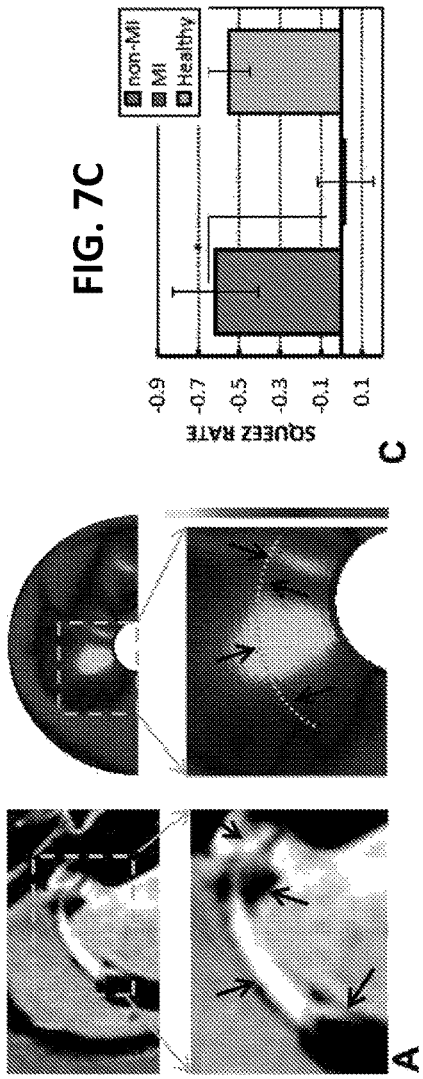
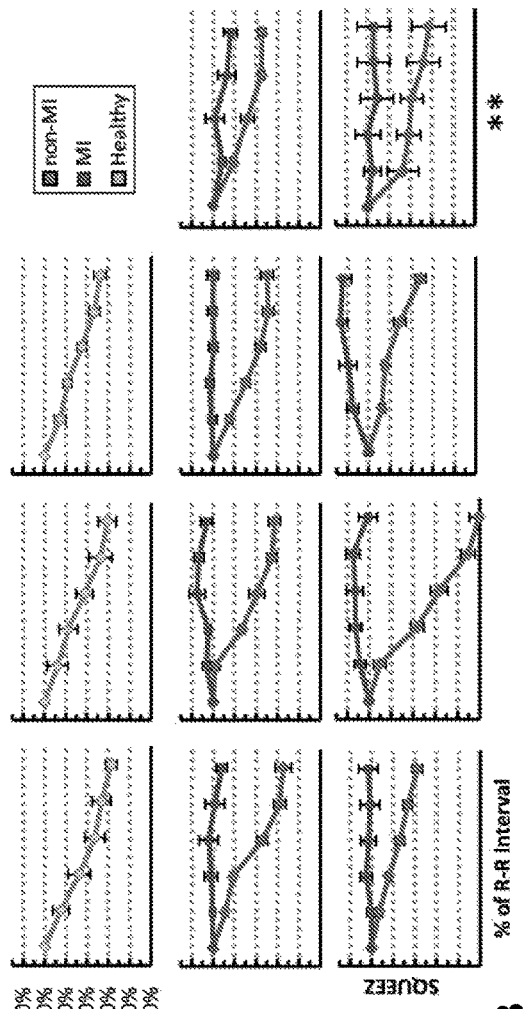
FIG. 7A
FIG. 7B
FIG. 7C

METHODS FOR EVALUATING REGIONAL CARDIAC FUNCTION AND DYSSYNCHRONY FROM A DYNAMIC IMAGING MODALITY USING ENDOCARDIAL MOTION

CROSS-REFERENCE TO RELATED APPLICATIONS

This application is a 35 U.S.C. § 371 U.S. national entry of International Application PCT/US2012/060007, having an international filing date of Oct. 12, 2012, which claims the benefit of U.S. Provisional Application No. 61/546,311, filed Oct. 12, 2011, the content of each of the aforementioned applications is herein incorporated by reference in their entirety.

GOVERNMENT LICENSE RIGHTS

This invention was made with government support under NIH R01 grants awarded by the National Institutes of Health (NIH). The government has certain rights in the invention.

FIELD OF THE INVENTION

The present invention relates generally to the use of imaging modalities. More particularly, the present invention relates to a method for evaluating cardiac function using an imaging modality.

BACKGROUND OF THE INVENTION

Coronary angiography is currently the most prevalent use of cardiac CT. Assessment of regional myocardial function has value in the diagnosis and monitoring of myocardial ischemia and myocardial dyssynchrony. Most mechanical analyses in the clinical setting are based on echocardiographic methods derived from two-dimensional motion data. Not all tomographic imaging modalities are capable of producing data with adequate temporal and spatial resolution for detailed regional function assessment. One difficulty with quantitative tomographic methods to estimate myocardial function is the inability to obtain adequate landmarks in the heart because of poor spatial resolution.

Cardiovascular magnetic resonance (CMR) tissue tagging, which is currently considered the reference method, is validated and accurate, but it is slow, has poor resolution in the slice selection direction, and requires extended breath holding, and its image analysis is time consuming because of the manual segmentation required to detect the myocardial borders. In addition, CMR imaging is still considered a contraindication in the rapidly growing population of patients with implanted pacemakers or implantable cardioverter-defibrillators.

Recent dramatic advances in cardiac CT imaging techniques allow for volumetric functional imaging of the entire heart with a few gantry rotations. The high temporal resolution acquisitions of the entire cardiac volume with wide-range detector CT allows a contrast bolus to be imaged over a short window in the heart cycle with very high spatial resolution, making visible fine anatomic structures, such as trabeculae, on the endocardial surface.

It would therefore be advantageous to provide a method for tracking the left ventricular (LV) wall motion and assessing local cardiac function in high-resolution volumetric cardiac CT images using fast, nonrigid, surface registration algorithms that match geometric features of the surface over time.

SUMMARY OF THE INVENTION

The foregoing needs are met, to a great extent, by the present invention, wherein in one aspect, a method for assessment of function of a region of interest, with sizes ranging from a few voxels to the whole heart, of a subject's heart includes acquiring an image sequence for the region of interest of the subject's heart using an imaging modality and inputting the image sequence into a processor configured to execute steps. The steps executed by the processor include determining a binary volume for each three-dimensional image (volume) of the image sequence and creating a triangular mesh representing an endocardial boundary for the region of interest of the subject's heart. The processor is also configured to calculate a shape metric such as the shape index value for the triangular mesh and use the shape index value along with coordinates of the region of interest of the subject's heart in a non rigid registration algorithm such as coherent point drift (CPD) to obtain a displacement map of the region of interest. This is done by tracking the motion of conserved topological features on this endocardial mesh for at least two time points. The displacement map is used to calculate trajectories of individual points on the region of interest of the subject's heart to obtain a mesh having corresponding triangular elements. A function of the ratio of areas of the corresponding triangular elements is calculated and a determination of cardiac function is made.

In accordance with an aspect of the present invention, the method also includes creating a visualization of the region of interest of the subject's heart. The visualization can take the form of one chosen from a group consisting of three-dimensional movie and a series of two-dimensional bull's-eye plots. The imaging modality is one of at least a tomography scanner, a computed tomography scanner, a magnetic resonance imaging device, or positron emission tomography scanner. The imaging modality can also take the form of a computed tomography scanner capable of producing image volumes with a temporal resolution within approximately 40 ms to approximately 75 ms at heart rates up to approximately 180 beats per minute using multi-beat segmented reconstruction algorithms.

In accordance with another aspect of the present invention the method includes calculating at least one of endocardial strain, cardiac torsion, and directional strain using the displacement map. The image sequence can be under both rest and stress conditions. Stress is inducible by exercise or drugs. Further, the shape index value uses the algorithm $$SI = \frac{2}{\pi}\arctan\frac{k_1 + k_2}{k_1 - k_2}$$

Where, $k_1$ and $k_2$ are principal curvatures of the surface. Additionally, the function of the ratio of areas of the corresponding triangular elements is calculated using $$SQUEEZ(v, t) = \sqrt{\frac{A(v, t)}{A(v, 0)}}$$

The region of interest of the subject's heart comprises a left ventricle, and the subject can be any one of but is not limited to the human, ape, monkey, cat, dog, pig, rodent, livestock, and other mammals. Also, the number of three-dimensional images (or volumes) in the image sequence is at least 2.

In accordance with another aspect of the present invention a system for assessment of function of a region of interest of a subject's heart includes an imaging modality configured for acquiring an image sequence for the region of interest of the subject's heart and a processor configured to execute steps. The steps executed by the processor calculating a shape index value for a triangular mesh representing an endocardial boundary for the region of interest of the subject's heart and using the shape index value along with coordinates of the region of interest of the subject's heart in a nonrigid registration algorithm such as coherent point drift (CPD) to obtain a displacement map of the region of interest. The processor is also used to calculate trajectories of individual points on the region of interest of the subject's heart to obtain a mesh having corresponding triangular elements using the displacement map. Another step includes calculating a function of the ratio of areas of the corresponding triangular elements and yet another includes making a determination of cardiac function.

In accordance with still another aspect of the present invention, the processor is configured to create a visualization of the region of interest of the subject's heart. The visualization takes the form of a three-dimensional movie or a series of two-dimensional bull's-eye plots. The imaging modality takes the form of a tomography scanner, a computed tomography scanner, a magnetic resonance imaging device, or positron emission tomography scanner. Alternately, the imaging modality comprises a computed tomography scanner capable of producing image volumes with a temporal resolution within approximately 40 ms to approximately 75 ms at heart rates up to approximately 180 beats per minute using multi-beat segmented reconstruction algorithms. The processor is configured to calculate at least one of endocardial strain, cardiac torsion, and directional strain using the displacement map and can acquire the image sequence under both rest and stress conditions. This stress condition can be induced by exercise or by using a drug. The processor can also be configured to calculate the shape index value using an algorithm $$SI = \frac{2}{\pi}\arctan\frac{k_1 + k_2}{k_1 - k_2}$$

The function of the ratio of areas of the corresponding triangular elements is calculated using $$SQUEEZ(v, t) = \sqrt{\frac{A(v, t)}{A(v, 0)}}$$

The area of interest of the subject's heart can be the left ventricle and the subject can be any one of but is not limited to human, ape, monkey, cat, dog, pig, rodent, livestock, or other mammal. Additionally, the number of three-dimensional images (volumes) in the image sequence comprises at least 2.

BRIEF DESCRIPTION OF THE DRAWINGS

The accompanying drawings provide visual representations which will be used to more fully describe the representative embodiments disclosed herein and can be used by those skilled in the art to better understand them and their inherent advantages. In these drawings, like reference numerals identify corresponding elements and:

FIGS. 3A-3F illustrate images representing the results of steps of a method for determining regional cardiac function according to an embodiment of the present invention.

FIGS. 7A-7C illustrate image and graphical views of resultant images and graphs created in the course of the execution of a method for determining regional cardiac function according to an embodiment of the present invention.

DETAILED DESCRIPTION

Figure 1:
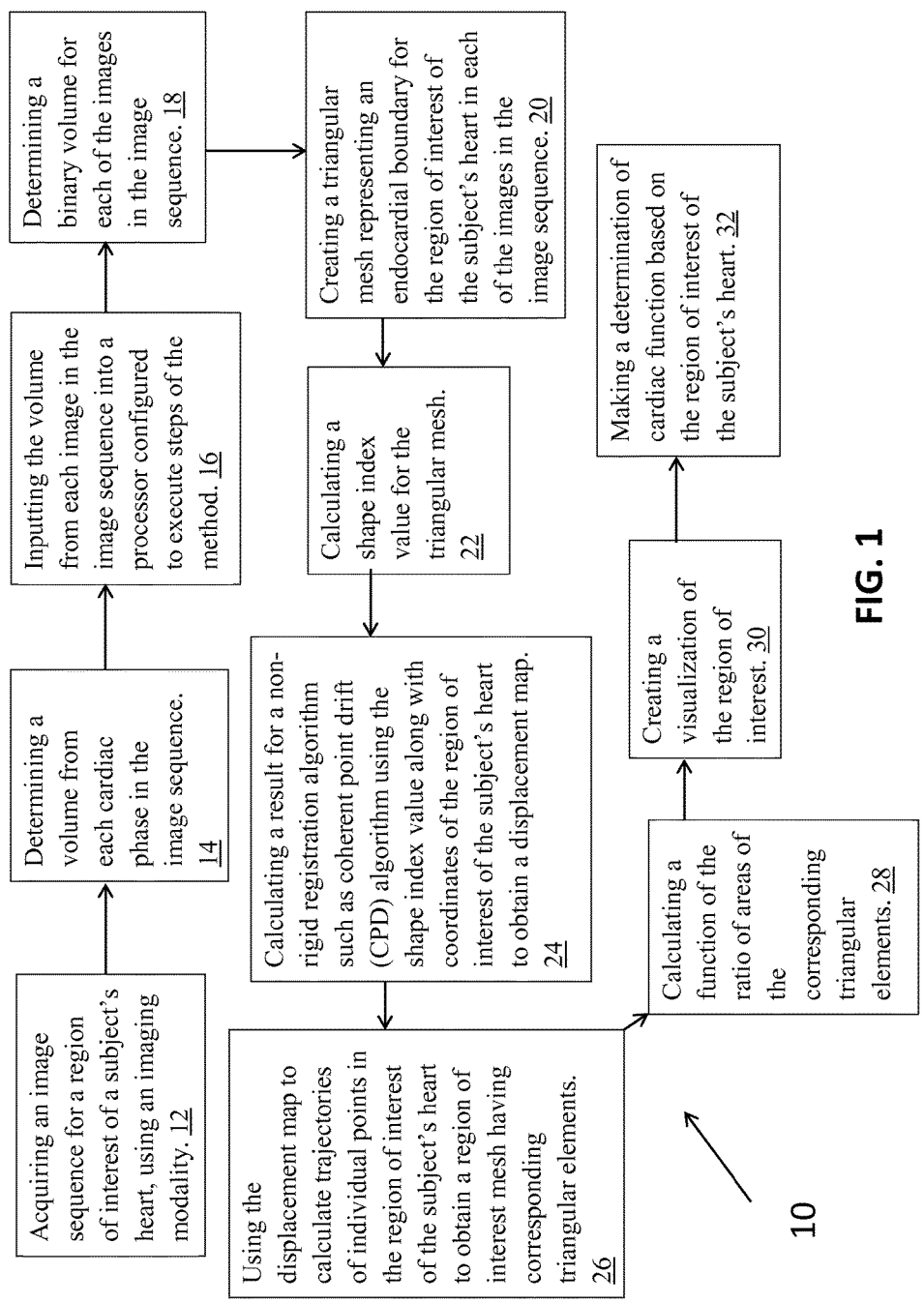
FIG. 1 illustrates a flow diagram of a method for determining regional cardiac function according to an embodiment of the present invention.

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

An embodiment in accordance with the present invention provides a method and system for evaluating regional cardiac function and dyssynchrony from an imaging modality using endocardial motion. In the method and system, an imaging modality such as a CT scanner is used to obtain an image sequence that is then processed using a computer program. The computer program is configured to create an endocardial mesh formed from triangular components that represents at least the region of interest of the subject's heart. From this endocardial mesh a displacement map can be modeled. The displacement map can be further analyzed to determine regional cardiac function using a SQUEEZ equation, and the displacement map can also be used to create visual representations of the function of the subject's heart.

As a part of the present invention, methods of assessment of cardiac function have been developed and implemented as software for execution on a computing device. The methods described herein can be implemented on the computing device either individually, or as any combination thereof. Indeed the methods can be used independently or all together to assess cardiac function. The methods are preferably embodied as a software program, which can be executed on a computing device, such as a desktop or laptop computer, tablet, smartphone, server, or other computing device known to or conceivable by one of skill in the art. Further, because this method is used in conjunction with an output from an imaging modality it is also possible that the software can be executed on a processor associated with any sort of imaging modality known to one of skill in the aft, such as a MRI scanner, a tomography scanner, a computed tomography scanner, or a PET scanner. The software program can be stored on any suitable computer readable medium known to or conceivable by one of skill in the art. Preferably, the software is written in Matlab and C++, but it should be noted that any suitable software platform known to or conceivable by one of skill in the art could also be used.

FIG. 1 illustrates a flow diagram of a method in accordance with an embodiment of the present invention. In the method 10 a step 12 includes acquiring an image sequence for a region of interest of a subject's heart, using an imaging modality. Step 14 includes determining a volume from each cardiac phase in the image sequence, and step 16 includes inputting each three-dimensional image (volume) in the image sequence into a processor configured to execute steps of the method described herein. The processor can take the form of a device and computer readable medium described previously, or any other suitable device and medium known to one of skill in the art.

More particularly, with respect to FIG. 1, the processor is configured to execute a step 18, which includes determining a binary volume for each of the volumes in the image sequence. Step 20 includes creating a triangular mesh representing an endocardial boundary for the region of interest of the subject's heart in each of the volumes in the image sequence. Another step, 22, includes calculating a shape index value for the triangular mesh and step 24 includes calculating a result for a non-rigid registration algorithm e.g. coherent point drift (CPD) using the shape index value along with coordinates of the region of interest of the subject's heart to obtain a displacement map. Step 26 includes using the displacement map to calculate trajectories of individual points in the region of interest of the subject's heart to obtain region of interest meshes at various cardiac phases having corresponding triangular elements. In step 28 a function of the ratio of areas of the corresponding triangular elements is calculated, and in step 30 a visualization of the region of interest is created. Additionally, step 32 includes making a determination of cardiac function based on the region of interest of the subject's heart.

Figure 2:
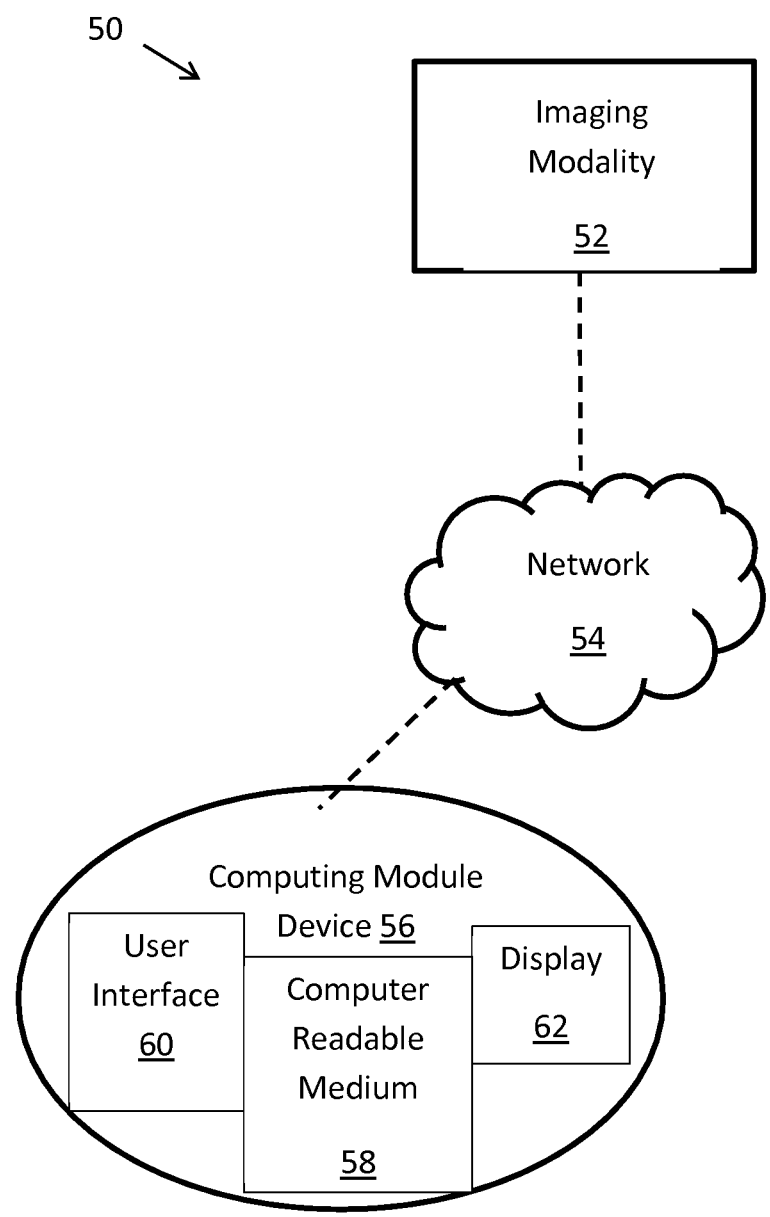
FIG. 2 illustrates a schematic diagram of a system for determining regional cardiac function according to an embodiment of the present invention.

In order to further illustrate the steps of the method described with respect to FIG. 1, above, FIG. 2 illustrates a schematic diagram of the system 50 used to execute the method. The system 50 includes an imaging modality 52, and it should be noted that any suitable imaging modality known to or conceivable by one of skill in the art can be used to obtain images of the subject's heart. For instance, the imaging modality can take the form of a tomography scanner, a computed tomography scanner, a magnetic resonance imaging device, or positron emission tomography scanner. Images making up an image sequence taken with the imaging modality 52 can be transferred via a network 54, such as a local area network, the internet, a server, or any other suitable networking construct known to or conceivable by one of skill in the art, to a computing device 56. Alternately, the computing device 56 can be a separate device connected to the imaging modality 52 using a hard wired connection.

Further, with respect to FIG. 2, the computing device 56, preferably, includes a computer readable medium 58 or other executable disc known to one of skill in the art. The computer readable medium contains code such that the method described herein can be executed and used to determine cardiac function. The computer readable medium 58 can also include a user interface 60 and a display 62 such that an operator can interact with the system 50 in order to input any necessary values or configure the functionality of the program as well as view the results of the method executed by the computing device 56. The display can take the form of a computer screen, tablet computing device, smartphone, television, or other display device known to one of skill in the art. The display 62 preferably is configured such that the results of the execution of the method can be visualized as a three-dimensional movie or a series of two-dimensional bulls-eye (polar) plots.

Figure 4:
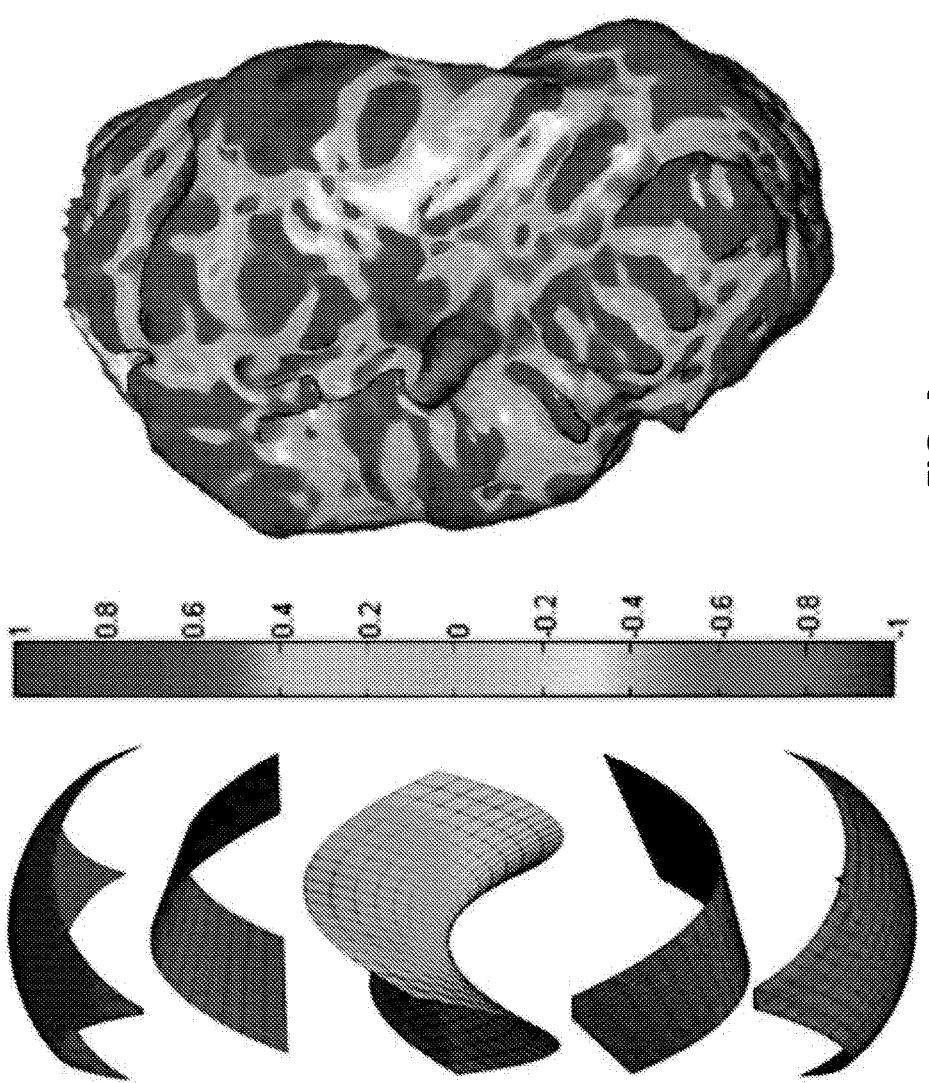
FIG. 4 illustrates a graphical view of shape index (SI) values for different surface shapes according to an embodiment of the present invention.

More particularly with respect to the method and the execution thereof, the motion of the area of interest of the subject's heart is tracked. In the example included, below, the area of interest takes the form of the left ventricle, although other areas of the heart could also be mapped. The motion is tracked by calculating trajectories for points on the triangles that form an endocardial mesh that represents each endocardial surface of the subject's heart. It should be noted that each endocardial surface should contain the same number of triangles, with a 1:1 correspondence between the vertices throughout the cardiac cycle. The points on the triangles are tracked from end diastole (ED) to end systole (ES). This is accomplished by choosing a template mesh and warping it onto a target mesh such that every triangle on the template mesh has a corresponding triangle on the target mesh, as illustrated in FIGS. 3D and 4. A non-rigid point registration algorithm referred to as coherent point drift (CPD) is used to execute the surface warping. CPD is a probabilistic method used for non-rigid surface registration in which surface points are forced to move coherently as a group to preserve the topological structure of the point sets. The coherence constraint was imposed by regularizing the displacement field and using variational calculus to derive the optimal warping. A fast implementation of CPD, based on the fast Gaussian transform, can preferably be used to reduce the computational burden associated with high resolution image data.

To match the anatomy through surface warping, the homologous anatomic features and their correspondences are identified. Therefore, features engraved on the endocardial surface by fine anatomic structures, such as trabeculae and papillary muscles, are encoded using a scale-dependent local shape measure termed shape index (SI) and incorporated in the warping algorithm to further improve the accuracy of the method. More specifically, the SI is a curvature based measure, and for each point is defined by $$SI = \frac{2}{\pi} \arctan \frac{k_1 + k_2}{k_1 - k_2}$$

where $k_1$ and $k_2$ are the principal (signed maximum and minimum) curvatures at that point. FIG. 4 illustrates SI values for different surface shapes. For a saddle point, $k_1=-k_2$; and thus, SI=0. For a spherical surface, $k_1=k_2\neq 0$, and the if curvatures are negative and +1 if curvatures are positive, corresponding to a spherical cup and cap, respectively. For a valley, $k_1=0$, and $k_2$ can have any negative value (by definition $k_1 \geq k_2$); thus, as long as $k_2$ is non-zero $$SI = \frac{2}{\pi}\arctan\frac{+k_2}{-k_2} = -0.5$$

The same holds true for a ridge, which will have an SI value of 0.5. The intermediate SI values correspond to when these shapes are smoothly warped to one another. It should also be noted that SI is stretch invariant. As mentioned above, surface features (e.g. ridges and valleys) will have a certain SI value solely based on their shape and not on their curvatures (i.e. steepness). Therefore, as long as the topology of the surface does not change under compression or stretch, the anatomic features, such as ridges and valleys on the endocardial surface, will retain their SI values. Because of this SI is a useful tool for encoding endocardial features.

Furthermore, the output of the CPD algorithm is a displacement field that is used to calculate measures of local cardiac function. A measure of local cardiac function, called Stretch Quantifier of Endocardial Engraved Zones (SQUEEZ) is defined as, $$SQUEEZ(v,t) = \sqrt{\frac{A(v,t)}{A(v,0)}}$$

where $A(v,0)$ is the area of the small triangular patch (v) on the endocardial Mesh at ED and $A(v, t)$ is the area of that same patch at time t. SQUEEZ is calculated for each triangular patch on the surface, resulting in a high-resolution local cardiac function map of the area of interest, such as the left ventricle.

FIGS. 3A-3F further illustrate modeled images of the proposed method described with respect to FIG. 1. FIG. 3A illustrates a cropped axial image, in this case a CT image, of an area of interest of the heart, particularly a left ventricle. FIG. 3B illustrates a visual representation of the blood pool segmented from the volume by thresholding. FIG. 3C illustrates an image of an endocardial surface extracted from the segmented images (inferolateral wall facing the viewer). FIG. 3D illustrates shape index values calculated to encode the features engraved by the trabecular structures on the endocardial surface. Coherent point drift algorithm is used to find the correspondence between the endocardial features at ED (left), used as a template, and other systolic phases (right), used as targets. FIG. 3E illustrates a diagram of CPD warping results in endocardial meshes with corresponding triangles. SQUEEZ is used to calculate the corresponding triangle at different cardiac phases, for each triangle on the ED endocardial surface mesh. A(0) is the area of the triangle at ED, and A(t) is the area at cardiac phase t. SQUEEZ is the square root of the ratio of the area of a triangle on the endocardial surface at a systolic phase to its area at ED. Additionally, FIG. 3F illustrates exemplary SQUEEZ maps calculated for every triangle on the endocardial surface at 5 cardiac phases from ED to ES.

In addition to the method described above, endocardial strain, cardiac torsion, directional strain and other similar metrics, known to or conceivable by one of skill in the art, can also be calculated in addition to the SQUEEZ metric. The imaging modality can be engaged both at rest and under stress, or alternately, under low and high heart rates. Regional cardiac function metrics are calculated from rest and stress scans and compared against each other to detect pathological cardiac regions and assess myocardial contractility quantitatively.

Also, stress can be induced through exercise such as using a treadmill, recumbent bicycle, or other similar device or through another method such as administering dobutamine or other drug. This method eliminates the need for administration of a dose of radiation, as is used in current conventional stress tests. Additionally, the method can be enhanced using a new generation of CT scanners that are capable of producing images with high temporal resolution (40-75 ms) at heart rates as high as NO bpm, using multi-beat segmented reconstruction algorithms. This provides sufficient temporal resolution and image quality to perform such a cardiac stress test. However, it is conceivable that other suitable scanning machinery is known to those of skill in the art or could be conceived in the future.

EXAMPLE

The following example is included merely as an illustration of the present method and is not intended to be considered limiting. This example is one of many possible applications of the methods described above. Any other suitable application of the above described methods known to or conceivable by one of skill in the art could also be created and used. While this example is directed to analysis of left ventricular function, any suitable region of interest can be studied.

Pigs with chronic myocardial infarctions (MIs) were used in the experiment. Briefly, MI was induced by engaging the left anterior descending coronary artery (LAD) with an 8F hockey stick catheter under fluoroscopic guidance. Then, a 0.014-in angioplasty guidewire was inserted into the LAD, and a 2.5×12-mm Maverick balloon (Boston Scientific) was inflated to 4 atm just distal to the second diagonal branch of the LAD. After 120 minutes, occlusion of the vessel was terminated by deflating the balloon, and restoration of flow in the LAD was confirmed by angiography. CT and MRI studies were performed ≈130 to 180 days after MI induction. A total of 11 animals were studied (7 chronic MI, 1 acute MI, and 3 healthy).

Each animal was scanned with electrocardiographic monitoring using a 0.5-mm×320-row detector scanner (Aquilion ONE; Toshiba Medical Systems Corporation). Animals received intravenous metoprolol (2-5 mg), amiodarone (50-150 mg), or both to achieve a heart rate of <100 beats/min. After scout acquisition, a 50- to 60-mL bolus of iodixanol (320 mg iodine/mL; Visipaque; Amersham Health) was injected intravenously, and a first-pass cardiac perfusion scan for the entire cardiac cycle was performed. During CT acquisition, respiration was suspended, and imaging was performed using a retrospectively gated CT protocol with the following parameters: gantry rotation time, 350 ms; temporal resolution, up to 58 ms using multi-segment reconstruction; detector collimation, 0.5 mm×320 rows (isotropic voxels, 0.5×0.5×0.5 mm3); tube voltage, 120 kV; and tube current, 400 mA. One infarcted data set was acquired using x-ray tube current modulation of 10% of the maximum, with the maximum current at only the 75% time point of the R-R interval. Images were reconstructed at every 10% of the R-R interval in systole using a standard kernel (FC03), QDS+ noise reduction filter, and a multi-segment (3-5 beats) reconstruction algorithm. Electrocardiographic editing to account for arrhythmias was performed when necessary. In addition, a set of low-dose, prospectively gated scans (120 kV and 20 mA at 0% and 50% of R-R) along with a high-dose (120 kV and 400 mA) retrospectively gated scan were acquired for 1 animal to assess the feasibility of tube current reduction and prospective gating for cardiac function analysis.

In vivo CMR images were acquired using a 3T MR scanner (Achieva; Philips) with a 32-element cardiac phased array. Myocardial viability was visualized using late gadolinium enhancement images acquired 20 to 25 minutes after intravenous injection of a double dose of gadolinium diethylenetriaminepentaacetic acid (0.2 mmol/kg body weight) (Magnevist; Berlex). A three-dimensional, ECG-triggered, independent respiratory navigator-gated, breath-hold, phase-sensitive inversion recovery gradient echo imaging pulse sequence was used. Imaging field of view was 24×24×12 cm3, with an imaging matrix of 200×195×30, yielding an acquired voxel size of 1.20×1.23×4.0 mm3 reconstructed to 0.91×0.91×2.0 mm3 Other relevant imaging parameters were as follows: flip angle, 15°; repetition time, 5.3 ms; echo time, 2.6 ms; and receiver bandwidth, 289 Hz/pixel.

For each systolic cardiac phase, the blood in the LV was segmented from the myocardium by thresholding the voxel intensities roughly between 200 and 650 Hounsfield units. After manually pruning the coronaries; aorta; and, in some data sets, the right ventricle (using the Medical Image Processing, Analysis, and Visualization program available from the National Institutes of Health at http://mipav.cit.nih.gov), a triangulated mesh representing the endocardial surface was extracted from the boundary surface of the LV blood cast, as illustrated in FIGS. 3A-3C and 3E. All computations, unless specified otherwise, were done using Matlab (MathWorks Inc) software. To compare the results of the proposed algorithm to existing CT wall motion tracking software, the data sets were analyzed using Vitrea fX software (Vital Images). These images were then processed using the method described above, particularly with respect to FIG. 1.

For the data pool obtained from the 11 animals, 2-tailed paired Student t-test statistical analyses were performed on the SQUEEZ value and the slope of SQUEEZ versus time to assess the difference in the means of these parameters in healthy and infarcted regions. The accuracy of the registration algorithm was evaluated using the mean of the minimum pairwise Euclidean distance between the target and the warped data sets (ie, for each point on the template mesh, the Euclidean distance to every point on the warped mesh is calculated, and the minimum is chosen). The mean±SD of the minimum distances is reported.

Figure 5:
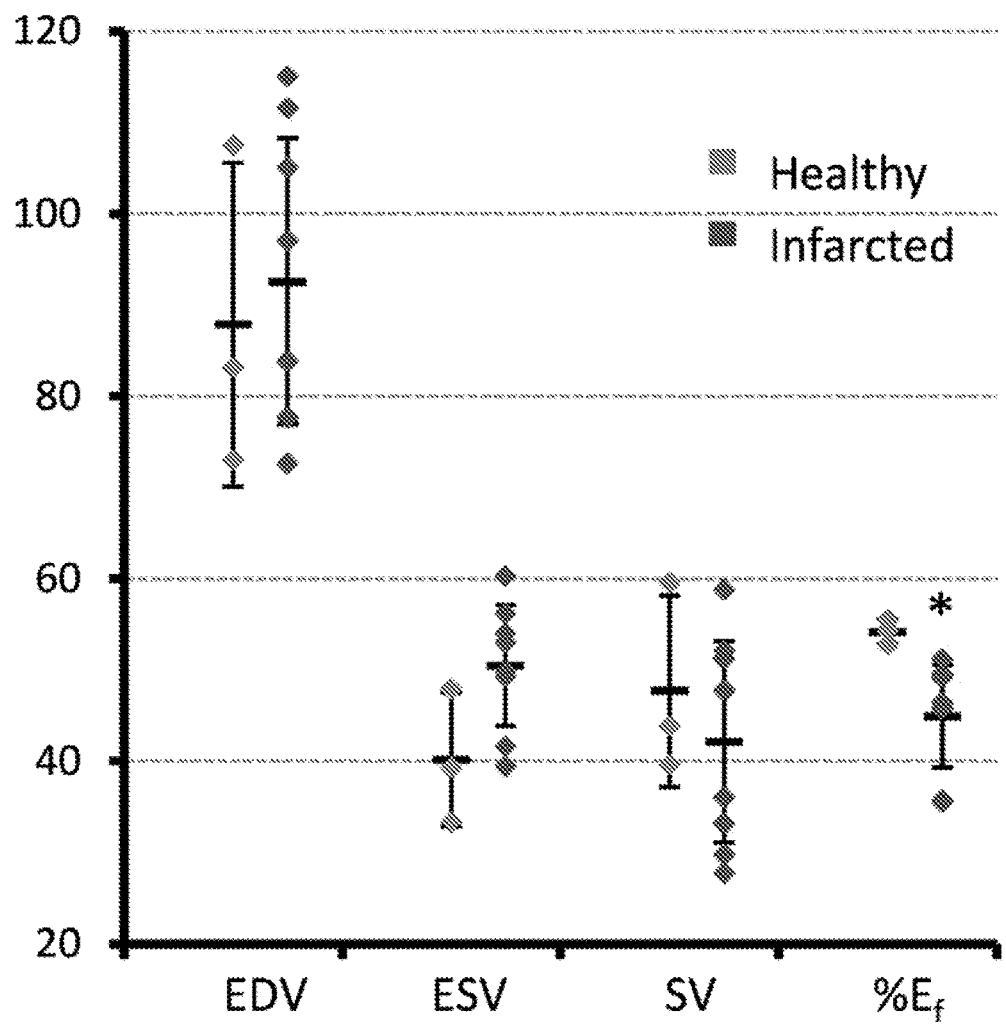
FIG. 5 illustrates a graphical view of global left ventrical function measures for healthy and infarcted subjects according to an embodiment of the present invention.

To evaluate resting LV function, the blood pool of the LV was segmented in the ED and ES phases in the three-dimensional volume and ED volume, ES volume, stroke volume, and ejection fraction were calculated for the LV, as illustrated in FIG. 5. SQUEEZ values were measured in healthy and infarcted animals at different cardiac phases, as illustrated in FIGS. 6A and 6B and different locations of infarcted and remote myocardium as detected by contrast-enhanced MRI, as illustrated in FIGS. 7A-7C.

Further, FIG. 5 illustrates a graphical representation of global left ventricle function measures for healthy (n=3) and infarcted (n=8) pigs. For healthy versus infarcted pigs, respectively, EDV is 87.8±17.7 versus 92.5±15.6 mL; ESV, 40.1±7.3 versus 50.4±6.6 mL; SV (EDV−ESV), 47.6±10.5 versus 42.0±11.0 mL; and % Ef (SV/EDV), 54.1±1.3% versus 44.9±5.6%. The bars and whiskers indicate the mean±SD of the quantities, respectively. EDV indicates end-diastolic volume; Ef, ejection fraction; ESV, end-systolic volume; SV, stroke volume. *$P<0.05$.

Figure 6A:
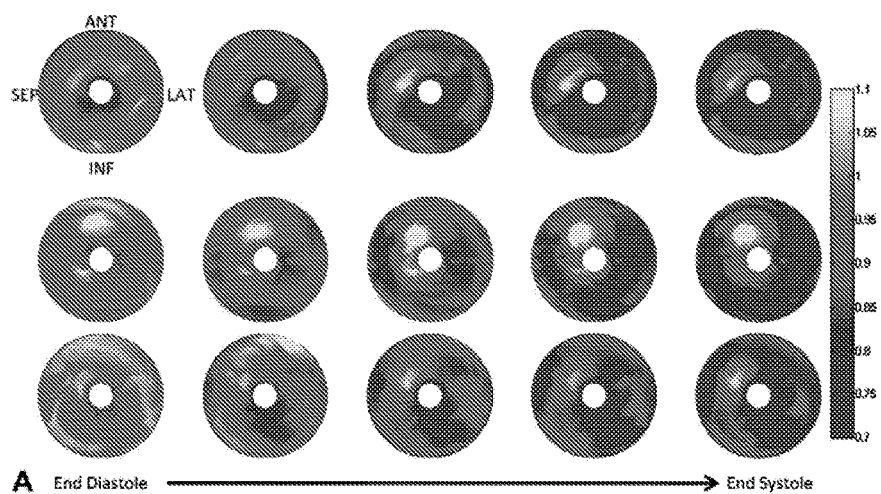
FIGS. 6A and 6B illustrate bull's-eye plots of the SQUEEZ values for three typically infarcted and 3 typically healthy animals according to an embodiment of the present invention.
Figure 6B:
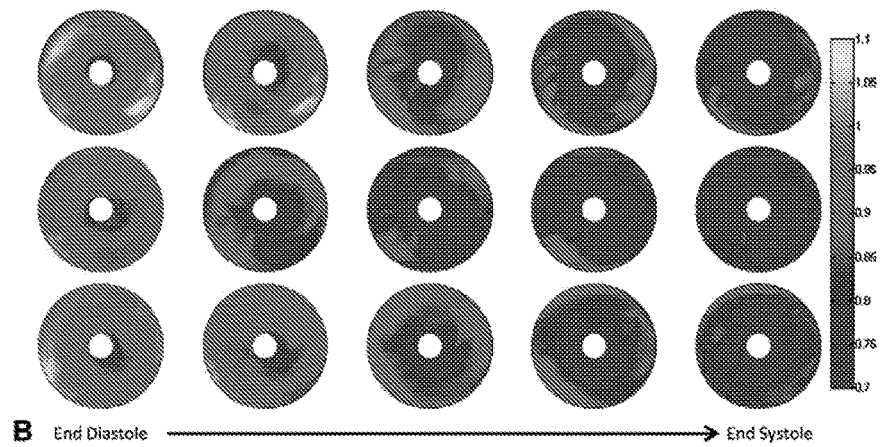

FIGS. 6A and 6B illustrate bull's-eye plots of the SQUEEZ values for 3 typical infarcted (FIG. 6A) and 3 healthy animals (FIG. 6B) from end diastole to end systole at 10% R-R intervals. Infarcted animals show abnormal stretching of the endocardium in LAD coronary artery territory (anterior and anteroseptal segments), which is consistent with the infarction model (LAD coronary artery occlusion after the second diagonal) used in this study. SQUEEZ indicates Stretch Quantifier for Endocardial Engraved Zones; LAD, left anterior descending.

FIGS. 7A-7C illustrate MRI results for this example. FIG. 7A illustrates a short-axis phase-sensitive inverted recovery MRI of an animal with an anterior/anteroseptal heterogeneously infarcted region (left). The infarcted region has characteristic high signal intensity. End-systolic SQUEEZ bull's-eye plot of the same animal (right). The short-axis image on the left approximately corresponds to the SQUEEZ values along the dashed arc. The infarcted subregions in the MRI correspond to the regions detected in the SQUEEZ plot, depicted by the arrows. Shown from left to right is a section with some loss of function, a section with complete loss of function that shows wall expansion, a small section with some contractility, and a fourth subregion with loss of function. FIG. 7B illustrates time plots of the average SQUEEZ values for healthy, MI, and non-MI regions in systole for 3 healthy and 7 infarcted pigs. The regions were chosen to be roughly the size of segments in the American Heart Association 17-segment model. All infarcted pigs showed significant differences in SQUEEZ for MI and non-MI regions ($P<0.0001$). FIG. 7C illustrates average SQUEEZ rate values calculated by averaging over the slopes of lines fitted to the curves in FIG. 7B. SQUEEZ rate is significantly different between MI and non-MI regions in infarcted hearts ($P<0.0001$). There was no significant difference between non-MI regions in the infarcted hearts and the same regions chosen in the healthy hearts. MI indicates myocardial infarction.

The accuracy of the nonrigid registration algorithm was evaluated using the mean of the minimum Euclidean distance between the target and warped surfaces evaluated at all points. Over the 11 animals analyzed by our method, there was a subpixel average error of 0.6±0.4 pixels (0.3±0.2 mm). All the triangular patches on the meshes had sides ≥1 pixel.

SQUEEZ was calculated for every point on the LV endocardial surface at each cardiac phase. All infarcted animals showed abnormal stretching in the LAD territory, which was consistent with the infarct model used in this example. One animal showed 2 distinct MI zones, and this was confirmed by examining the CMR image, which showed a secondary MI in the inferior wall.

Contrast-enhanced CMR images were used to verify the location of the infarcted regions detected in SQUEEZ maps, as illustrated in FIG. 7A. Points were selected on regions of the endocardial surface near the MI zones as defined by the contrast-enhanced CMR images. Approximately the same number of points were selected in a remote region of the heart with no sign of MI, as illustrated in FIG. 7B. The size of the selected regions roughly corresponded to that of 1 LV segment in the 17-segment American Heart Association model.

The average SQUEEZ value was calculated for each zone and showed a significant difference (P<0.0001) between MI and non-MI regions in infarcted animals, as illustrated in FIG. 7B. For healthy animals, a region on the lateral wall was chosen corresponding to the remote non-MI region selected in infarcted animals. The SQUEEZ values for the non-MI region in the infarcted hearts and the regions chosen in the healthy hearts were not significantly different.

In addition to SQUEEZ, the rate of change in SQUEEZ also showed a significant difference (P<0.0001) between MI and non-MI regions in the infarcted animals, as illustrated in FIG. 7C and no difference was found between the same lateral regions in healthy and non-MI regions. Non-MI regions showed an average SQUEEZ rate of ≈0.6±0.2, whereas the MI zones had a rate of ≈0±0.1, showing little or no stretch or contraction.

The SQUEEZ time plots for the tube current modulated data set showed higher SDs because of increased noise levels. However, the difference between MI and non-MI regions was still significant, and the trend of the plots were similar to those of the high-dose data sets, as illustrated in FIG. 7B.

Figure 8:
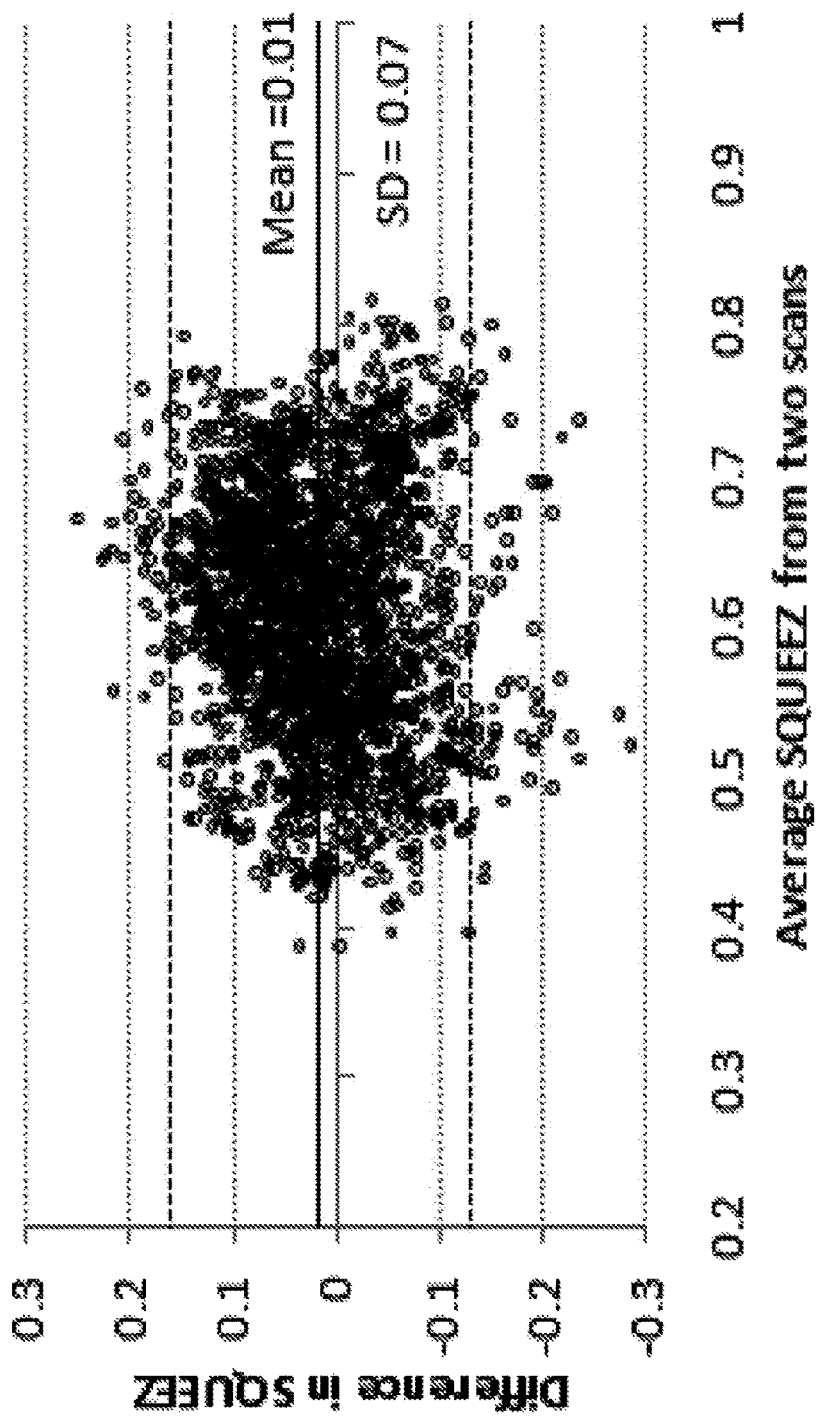
FIG. 8 illustrates a graphical view of a comparison between scans taken in the course of the execution of a method for determining regional cardiac function according to an embodiment of the present invention.

The SQUEEZ map was calculated for the low-dose prospectively gated data set and compared to the SQUEEZ of the high-dose retrospectively gated data set at 50% of the R-R interval. The difference between the SQUEEZ maps was computed, and is represented in the graph of FIG. 8. The results show low bias (0.01; 95% CI, −0.12 to 0.15) between the high-dose retrospective and the low-dose prospective scans. The differences could be attributed not only to the increased noise due to lower tube current, but also to heart rate variations among the acquisitions. More experiments are going be carried out to fully investigate the effects of CT noise on the accuracy of SQUEEZ. Use of the low-dose prospective scan decreased the radiation dose by ≈10-fold. The low bias and 95% CI of the low-dose scan make the use of low-dose, prospectively gated CT for cardiac function very promising.

Regional ejection fraction (rEF) was calculated at ES for each cardiac segment using Vitrea fX software. The automatic segmentation of endocardial borders required manual correction, which took ≈150±15 minutes, as opposed to 4±2 minutes of operator interaction required in the proposed method. SQUEEZ values were averaged into the American Heart Association 16 segments and compared to 1-rEF values obtained from Vitrea fX. There was good correlation (r=0.81, P<0.001) for the 6 mid-cavity segments (segments 7-12), but no correlation was found in basal and apical segments in any of the data sets.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

Although the present invention has been described in connection with preferred embodiments thereof, it will be appreciated by those skilled in the art that additions, deletions, modifications, and substitutions not specifically described may be made without departing from the spirit and scope of the invention as defined in the appended claims.

What is claimed is:

1. A method for assessment of function of a region of interest of a subject's heart, comprising:
   receiving, by a processor, an image sequence for the region of interest of the subject's heart from an imaging modality,
   the imaging modality being one of:
      a computed tomography scanner,
      a magnetic resonance imaging device, or
      a positron emission tomography scanner;
   generating, by the processor, a three-dimensional image from each cardiac phase in the image sequence;
   determining, by the processor and based on generating the three-dimensional image from each cardiac phase in the image sequence, a binary volume for the three-dimensional image from each cardiac phase in the image sequence;
   creating, by the processor, a first set of triangular meshes, representing an endocardial boundary for the region of interest of the subject's heart, for the three-dimensional image from each cardiac phase in the image sequence;
   encoding, by the processor, features on an endocardial surface using a shape index value for the first set of triangular meshes,
   the features identifying anatomic structures;
   calculating, by the processor, a result for a non-rigid registration algorithm using the shape index value along with coordinates of the region of interest of the subject's heart in the three-dimensional image from each cardiac phase in the image sequence to obtain a displacement map of the region of interest of the subject's heart;
   using, by the processor, the displacement map to calculate trajectories of individual points on triangles of the first set of triangular meshes from end diastole to end systole to obtain a second set of triangular meshes, directed to the region of interest of the subject's heart, for the three-dimensional image from each cardiac phase in the image sequence,
   the first set of triangular meshes and the second set of triangular meshes having corresponding triangular elements;
   calculating, by the processor, a function of a ratio of areas for each of the corresponding triangular elements using $$SQUEEZ(v, t) = \sqrt{\frac{A(v, t)}{A(v, 0)}},$$

A(v,0) being an area of a triangular element (v), of the corresponding triangular elements, at the end diastole, and
   A(v,t) being the area of the triangular element (v) at time t; and
   creating, by the processor, a visualization of the region of interest of the subject's heart based on calculating the function of the ratio of the areas for each of the corresponding triangular elements,
   the visualization representing the function of the region of interest of the subject's heart.

2. The method of claim 1, wherein the visualization takes a form of one of a three-dimensional movie or a series of two-dimensional bull's-eye plots.

3. The method of claim 1, wherein the imaging modality comprises the computed tomography scanner, the computed tomography scanner being capable of producing images with a temporal resolution within approximately 40 ms to approximately 75 ms at heart rates up to approximately 180 beats per minute.

4. The method of claim 1, further comprising:
calculating at least one of endocardial strain, cardiac torsion, or directional strain.

5. The method of claim 1, further wherein the image sequence is associated with a rest condition and a stress condition.

6. The method of claim 5, further comprising:
inducing the stress condition via exercise.

7. The method of claim 5, further comprising:
inducing the stress condition using a drug.

8. The method of claim 1, wherein the region of interest of the subject's heart comprises a left ventricle.

9. The method of claim 1, wherein a quantity of three-dimensional images in the image sequence comprises at least 2 time frames.

10. The method of claim 1, further comprising:
providing, for display, the visualization.

11. A system for assessment of function of a region of interest of a subject's heart, comprising:
one or more processors configured to:
receive an image sequence for the region of interest of the subject's heart from an imaging modality,
the imaging modality being one of:
a computed tomography scanner,
a magnetic resonance imaging device, or
a positron emission tomography scanner;
generate a three-dimensional image from each cardiac phase in the image sequence;
determine, based on generating the three-dimensional image from each cardiac phase in the image sequence, a binary volume for the three-dimensional image from each cardiac phase in the image sequence;
create a first set of triangular meshes, representing an endocardial boundary for the region of interest of the subject's heart, for the three-dimensional image from each cardiac phase;
encode features on an endocardial surface using a shape index value for the first set of triangular meshes,
the features identifying anatomic structures;
calculate a result for a non-rigid registration algorithm using the shape index value along with coordinates of the region of interest of the subject's heart in the three-dimensional image from each cardiac phase in the image sequence to obtain a displacement map of the region of interest of the subject's heart;
use the displacement map to calculate trajectories of individual points on triangles of the first set of triangular meshes from end diastole to end systole to obtain a second set of triangular meshes having corresponding triangular elements;
calculate a function of a ratio of areas for each of the corresponding triangular elements using $$SQUEEZ(v, t) = \sqrt{\frac{A(v, t)}{A(v, 0)}},$$

A(v,0) being an area of a triangular element (v), of the corresponding triangular elements, at the end diastole, and A(v,t) being the area of the triangular element (v), at time t; and
create a visualization of the region of interest of the subject's heart based on calculating the function of the ratio of the areas for each of the corresponding triangular elements.

12. The system of claim 11, wherein the visualization takes a form of one of a three-dimensional movie or a series of two-dimensional bull's-eye plots.

13. The system of claim 11, wherein the imaging modality comprises the computed tomography scanner,
the computed tomography scanner being capable of producing images with a temporal resolution within approximately 40 ms to approximately 75 ms at heart rates up to approximately 180 beats per minute.

14. The system of claim 11, wherein the one or more processors are further configured to:
calculate at least one of endocardial strain, cardiac torsion, or directional strain.

15. The system of claim 11, wherein the one or more processors are further configured to:
process the image sequence under both a rest condition and a stress condition.

16. The system of claim 11, wherein the region of interest of the subject's heart comprises a left ventricle.

17. The system of claim 11, wherein the non-rigid registration algorithm comprises a coherent point drift (CPD) algorithm.

18. The system of claim 11, wherein a quantity of three-dimensional images in the image sequence comprises at least 2 time frames.

19. The system of claim 11, wherein the one or more processors are further configured to:
provide, for display, the visualization.

20. A non-transitory computer-readable medium storing instructions, the instructions comprising:
one or more instructions that, when executed by a processor, cause the processor to:
receive an image sequence for a region of interest of a subject's heart from one of:
a computed tomography scanner,
a magnetic resonance imaging device, or
a positron emission tomography scanner;
generate a three-dimensional image from each cardiac phase in the image sequence;
determine, based on generating the three-dimensional image from each cardiac phase in the image sequence, a binary volume for the three-dimensional image from each cardiac phase in the image sequence;
create a first set of triangular meshes, representing an endocardial boundary for the region of interest of the subject's heart, for the three-dimensional image from each cardiac phase;
encode features on an endocardial surface using a shape index value for the first set of triangular meshes,
the features identifying anatomic structures;
calculate a result for a non-rigid registration algorithm using the shape index value along with coordinates of the region of interest of the subject's heart in the three-dimensional image from each cardiac phase in the image sequence to obtain a displacement map of the region of interest of the subject's heart;
use the displacement map to calculate trajectories of individual points on triangles of the first set of triangular meshes from end diastole to end systole to obtain a second set of triangular meshes having corresponding triangular elements;

calculate a function of a ratio of areas for each of the corresponding triangular elements using $$SQUEEZ(v, t) = \sqrt{\frac{A(v, t)}{A(v, 0)}},$$

A(v,0) being an area of a triangular element (v), of the corresponding triangular elements, at the end diastole, and A(v,t) being the area of the triangular element (v) at time t; and create a visualization of the region of interest of the subject's heart based on calculating the function of the ratio of the areas for each of the corresponding triangular elements.

21. The non-transitory computer-readable medium of claim 20, wherein the one or more instructions, when executed by the processor, further cause the processor to:
calculate at least one of endocardial strain, cardiac torsion, or directional strain.

22. The non-transitory computer-readable medium of claim 20, wherein the one or more instructions, that cause the processor to receive the image sequence, further cause the processor to:
receive the image sequence during a rest condition and a stress condition.

* * * * *